United States Patent
Persson et al.

(10) Patent No.: US 8,386,049 B2
(45) Date of Patent: Feb. 26, 2013

(54) ADAPTIVE STAGED WAKE-UP FOR IMPLANTABLE MEDICAL DEVICE COMMUNICATION

(75) Inventors: Benjamin T. Persson, Sunnyvale, CA (US); Dorin Panescu, San Jose, CA (US); Dean Andersen, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 0 days.

(21) Appl. No.: 13/095,651

(22) Filed: Apr. 27, 2011

(65) Prior Publication Data
US 2011/0202113 A1 Aug. 18, 2011

Related U.S. Application Data

(62) Division of application No. 11/745,651, filed on May 8, 2007, now Pat. No. 7,957,813.

(51) Int. Cl.
*A61N 1/00* (2006.01)
(52) U.S. Cl. .......................... 607/60; 607/32
(58) Field of Classification Search .................... 128/903
See application file for complete search history.

(56) References Cited

U.S. PATENT DOCUMENTS

| | | | |
|---|---|---|---|
| 6,647,298 B2* | 11/2003 | Abrahamson et al. | 607/60 |
| 2005/0277999 A1* | 12/2005 | Strother et al. | 607/48 |
| 2006/0030903 A1* | 2/2006 | Seeberger et al. | 607/60 |

* cited by examiner

*Primary Examiner* — Carl H Layno
*Assistant Examiner* — Paula J Stice
(74) *Attorney, Agent, or Firm* — Steven M. Mitchell

(57) ABSTRACT

A communication wake-up scheme for an implantable medical device may involve repeatedly activating a receiver to determine whether an external device is attempting to establish communication with the implantable device. To reduce the amount of power consumed by the implantable device in conjunction with the wake-up scheme, the scheme may involve conducting preliminary RF signal detections as a precursor to conducting a full scan. In this way, power may be conserved since the more power intensive full scans may be performed less frequently. This preliminary detection of RF signals also may be adapted to reduce the number of full scans performed by the implantable device that do not result in communication with the external device. In some embodiments the adaptation involves adjusting one or more thresholds that are used in conjunction with the preliminary detection of RF signals. In some embodiments a wake-up scheme may involve scanning for signals using an initial RF band that is relatively wide, and then scanning for signals using narrower RF bands.

30 Claims, 9 Drawing Sheets

ADAPTIVE STAGED WAKE-UP FOR IMPLANTABLE MEDICAL DEVICE COMMUNICATION

PRIORITY CLAIM

This application is a Divisional Application of and claims priority and other benefits from U.S. patent application Ser. No. 11/745,651, filed May 8, 2007 entitled "ADAPTIVE STAGED WAKE-UP FOR IMPLANTABLE MEDICAL DEVICE COMMUNICATION," now issued as U.S. Pat. No. 7,957,813, incorporated herein by reference in its entirety.

TECHNICAL FIELD

This application relates generally to implantable medical devices, and to staged detection of communication signals.

BACKGROUND

Implantable medical devices may be employed in various applications. For example, an implantable cardiac device may perform one or more functions including sensing signals generated in the heart, pacing the heart to maintain regular contractions, and providing defibrillation shocks to the heart. Similarly, an implantable stimulation device may be used to apply stimulation signals to a patient's muscular tissue, neurological system, or some other area of the patient's body.

In practice, there may be a need to communicate with an implantable medical device after it has been implanted in a patient. For example, an external monitoring device located in a person's home, a doctor's office, a clinic, or some other suitable location may be used to retrieve information collected by and stored on the implanted medical device. In the case of an implantable cardiac device such information may include sensed cardiac activity that a treating physician may wish to analyze to determine the relative health of the patient. Similarly, an external programming device located in any of the above locations may be used by a treating physician to change the operating parameters of the implanted medical device. Such parameters may include, for example, the timing or magnitude of stimulation pulses generated by the implanted medical device.

In a typical implementation, an implantable medical device utilizes radio frequency ("RF") telemetry to communicate with an external device. Thus, the implantable medical device may include an RF transceiver that is adapted to transmit and receive the necessary RF signals. In such an implementation, however, it is generally desirable to leave the transceiver in a powered-off or low power state as much as possible since a transceiver typically consumes a relatively large amount of power. Here, it should be appreciated that the replacement of the battery in an implanted medical device involves a surgical procedure. Hence, long battery life is an important aspect of an implantable medical device.

Some types of implantable medical devices employ a wake-up scheme whereby an implantable medical device will periodically turn on its transceiver (e.g., its receiver) to determine whether an external device is attempting to communicate with the implantable medical device. For example, whenever an external device wishes to establish communication with an implantable device the external device periodically transmits polling messages (e.g., connection requests) over one or more designated RF channels. Each polling message may include information relating to establishing the communication such as, for example, an identifier that uniquely identifies the implantable medical devices.

Every time the transceiver is turned on it may then conduct a scan to determine whether the external device is transmitting polling messages. This may involve, for example, performing an ID scan that checks each RF channel for any messages that include the identifier of that particular implantable medical device. In the event such a signal is detected, the implantable medical device transmits an appropriate signal to establish communication with the external device.

In practice, a transceiver of an implantable medical device may still consume a relatively significant amount of power even when a conventional wake-up scheme is used. For example, scanning each RF channel for polling messages consumes a relatively large amount of power since the RF receiver must be enabled for a relatively long period of time to perform the search. Moreover, it is also desirable that an implantable medical device respond to polling messages within a relatively short period of time. For example, a treating physician would normally not wish to wait several minutes to establish communication with the implanted medical device. To achieve such a quick response time, however, the implantable medical device may need to perform its scans at relatively frequent intervals. Hence, a relatively large amount of power may be consumed due to the frequency of such scans.

Some forms of wake-up schemes employ staged detection to further reduce the amount of power consumed by the implantable medical device. Here, the implantable medical device may employ an early detection stage that triggers a more refined detection stage that analyzes any detected signals to determine whether the signals are from an external device that is attempting to establish communication with the implantable medical device. For example, one technique employs an initial energy "sniff" in the radio frequency channel or channels of interest. By starting a detection search with this low-level and relatively coarse energy assessment stage, the implantable medical device may bypass the relatively high power stage scan whenever a radio frequency signal is not present. In practice, the absence of such an RF signal will be the case for most of the lifetime of the implantable medical device. Hence, additional power savings may be achieved with this type of wake-up scheme.

SUMMARY

A summary of sample aspects of the disclosure or sample embodiments of an apparatus constructed or a method practiced according to the teachings herein follows. It should be appreciated that any references herein to "an" or "one" aspect or embodiment or to "some" aspects or embodiments are not necessarily referring to the same aspect or embodiment. Moreover, such references should be understood as meaning "at least one" aspect or embodiment.

The disclosure relates in some aspects to a wake-up scheme for determining whether an external device is attempting to communicate with an implantable medical device. Here, the implantable medical device may regularly "wake-up" it's receiver to scan for signals from the external device. In addition, the wake-up scheme may employ staged detection whereby the results of initial low-level scans may be used to trigger more thorough, higher-level scans.

In some embodiments signal detection-related parameters used for the low-level scans are adapted to improve the accuracy with which the low-level scans provide a preliminary indication of a valid communication attempt by an external device. For example, in some embodiments a property of a detected RF signal (e.g., amplitude, frequency, phase, or some other characteristic) is compared with a threshold to determine whether to invoke a higher-level scan. In this case, the threshold may be dynamically adapted based on how often the higher-level scans identify a valid communication attempt. For example, if a disproportionately high number of the higher-level scans do not identify a valid communication attempt, the threshold may be lowered such that in the immediate future a smaller percentage of the low-level scans may cause a high-level scan to be invoked. It should be appreciated that adaptation may be accomplished in a variety of ways other than by adjusting a threshold. For example, the amplification of the received RF signal could be increased such that the rate of successful channel detection increases as well. Power consumption associated with the wake-up scheme may thus be reduced as a result of a reduction in the number of high-level scans that do not result in the commencement of a communication session with the external device. Advantageously, as a result of the power savings achieved through the use of this technique, the implantable medical device may successfully search for RF signals more frequently. Consequently, the wake-up scheme may be employed to provide relatively long-range communication (e.g., in the medical implant communication service band) with relatively short connection delays.

Through the use of the above parameter adaptation technique the wake-up scheme may effectively adjust to ambient and other conditions. For example, a detection-related parameter may be adapted to account for background RF noise or other types of ambient noise, and to reduce the impact of the presence of other similar RF devices in the immediate area. Moreover, through the use of dynamic adaptation of a detection-related parameter, the wake-up scheme may adapt to changes in such conditions on a continual basis.

In some embodiments detection-related parameters may be adapted based on analysis of ambient conditions. For example, the implantable medical device and/or the external device may conduct regular scans to determine, for example, ambient RF energy levels within one or more RF bands of interest. Such information may then be used to, for example, increase or decrease a threshold under certain conditions.

In some embodiments detection-related parameters may be defined for particular locations, particular times of day, or other conditions. For example, the implantable medical device and/or the external device may conduct scans to characterize the ambient conditions at various locations and/or at certain times of day. This information may then be used to adjust the detection-related parameters at those times or whenever the implantable medical device is at those locations.

In some embodiments a staged detection technique involves using the result of an initial scan performed over a relatively wide frequency range to trigger additional scans over narrower frequency ranges. Here, the initial scan may scan over a bandwidth associated with all of the channels within which the external device may transmit signals. If a sufficient level of energy is detected during the initial scan, the implantable medical device may then perform more narrow scans over one or more subsets of those channels. In some embodiments this narrowing process may be repeated to eventually identify the specific channel over which the signals are being transmitted. Through the use of this or other similar staged detection techniques, the implantable medical device may efficiently identify a channel to be fully scanned or may identify a point in time when the full scan should be conducted.

BRIEF DESCRIPTION OF THE DRAWINGS

These and other features, aspects and advantages that may relate to the invention will be more fully understood when considered with respect to the following detailed description, appended claims and accompanying drawings, wherein:

Figure 1:
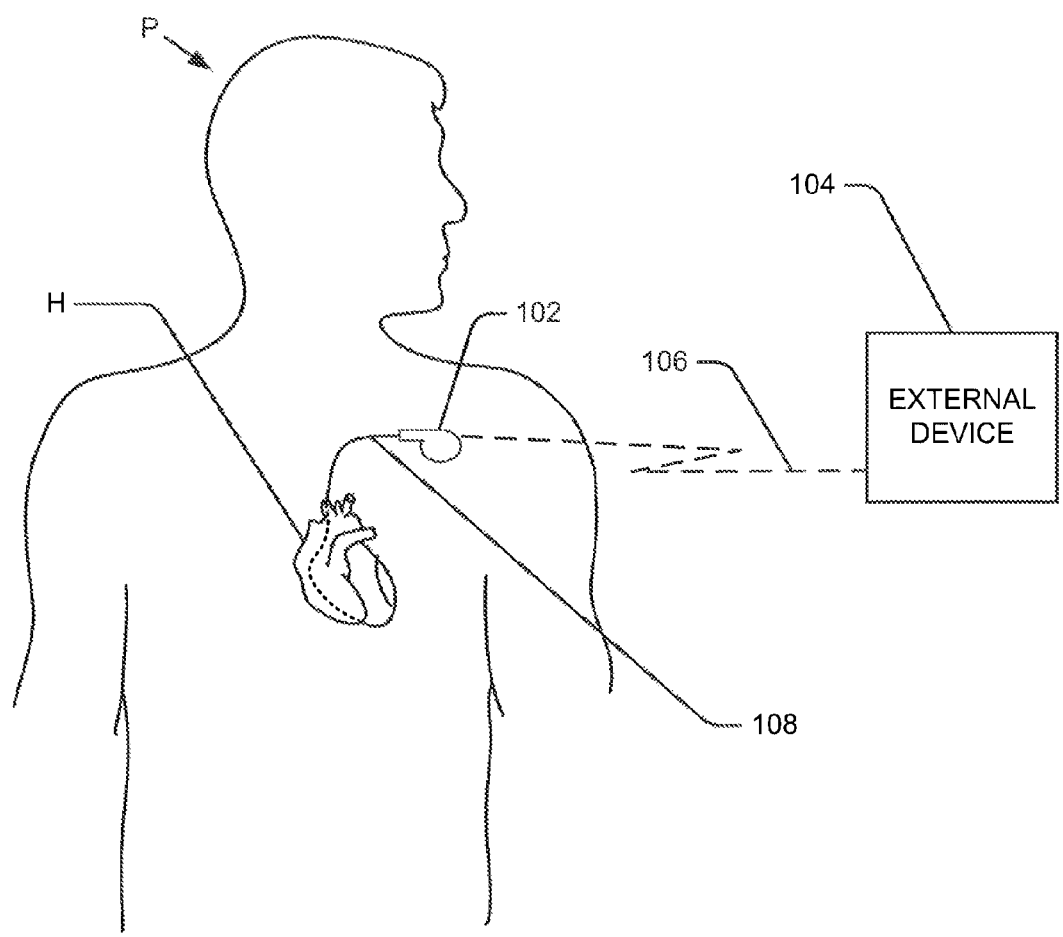
FIG. 1 is a simplified diagram of a communication system including an implantable medical device and an external device.

In accordance with common practice the various features illustrated in the drawings may not be drawn to scale. Accordingly, the dimensions of the various features may be arbitrarily expanded or reduced for clarity. In addition, some of the drawings may be simplified for clarity. Thus, the drawings may not depict all of the components of a given apparatus or method. Finally, like reference numerals may be used to denote like features throughout the specification and figures.

DETAILED DESCRIPTION

The invention is described below, with reference to detailed illustrative embodiments. It will be apparent that the invention may be embodied in a wide variety of forms, some of which may appear to be quite different from those of the disclosed embodiments. Consequently, the specific structural and functional details disclosed herein are merely representative and do not limit the scope of the invention. For example, based on the teachings herein one skilled in the art should appreciate that the various structural and functional details disclosed herein may be incorporated in an embodiment independently of any other structural or functional details. Thus, an apparatus may be implemented or a method practiced using any number of the structural or functional details set forth in any disclosed embodiment(s). Also, an apparatus may be implemented or a method practiced using other structural or functional details in addition to or other than the structural or functional details set forth in any disclosed embodiment(s).

FIG. 1 illustrates a simplified diagram of a communication system 100 including an implantable medical device 102 that is implanted within a patient P and a device 104 that is located external to the patient P. As represented by the line 106, the device 102 and the device 104 may communicate with one another via a wireless communication link 106.

FIG. 1 illustrates an example where the device 102 is an implantable cardiac device including one or more leads that are routed to the heart H of the patient P. For example, the device 102 may be a pacemaker, an implantable cardioverter defibrillator, or some other similar device. It should be appreciated, however, that the device 102 may take other forms. For example, the device 102 may be a neuro-stimulation device or some other type of implantable device.

The device 104 also may take various forms. For example, the device 104 may be a base station, a programmer, a home safety monitor, a personal monitor, a follow-up monitor, a wearable monitor, or some other type of device that is configured to communicate with an implantable device.

In a typical embodiment the communication link 106 is an RF link. In some embodiments the communication link 106 may operate within the medical implant communication service band. It should be appreciated, however, that the teachings herein may be employed in conjunction with other RF bands such as a band in the 2.45 GHz range or some other band. In other embodiments the communication channel 106 may take other forms including, for example, an inductive telemetry link.

The communication link 106 may be used to transfer information between the device 102 and 104 in conjunction with various applications such as surgical procedures, clinical visits, data acquisition, remote follow-up, remote home-monitoring, and portable or wearable patient monitoring/control systems. For example, when information needs to be transferred between the device 102 and 104 the patient P moves into a position that is relatively close to the device 104, or vice versa. As will be discussed in more detail below, the device 104 may then be configured to transmit periodic signals to the device 102 to initiate communication between the devices 102 and 104.

The device 102 implements a wake-up scheme for determining whether the device 104 is attempting to establish communication with the device 102. That is, a component (e.g., a transceiver) of the device 102 that is used for communicating with the device 104 may normally be turned off or set to a low power mode in some other manner. This component may then be turned on from time to time (e.g., periodically) to scan for signals from the device 104.

In some embodiments the wake-up scheme employs a staged detection scheme, whereby the result of a low-level scan is used to determine whether to conduct a high-level scan (e.g., a full scan). In some embodiments there may be several lower-level stages of detection to reduce the number of times that the relatively high power consumption, high-level detection stage is performed. In some embodiments each stage may have to succeed a specified number of times before advancement to the next level is allowed.

The detection scheme may be adaptive and dynamically adjust its parameters to increase the likelihood of detection of a legitimate signal and to reduce any penalties (e.g., increased power consumption) relating to any failed searches. Here, with either the success or the failure of a search at a given stage, parameters such as decision thresholds, amplification, or search intervals for that stage or any other detection stage may be adjusted accordingly. For example, the thresholds or amplification for the low-level scans may be adapted to reduce the number of full scans performed by the device 102 that do not result in communication with the device 104. Such an elevated or depressed state of detection sensitivity (as caused by the adjustment of a parameter) may be temporary and eventually timeout. That is, after the timeout the parameter may be returned to a prior setting (e.g., an original or default setting).

In some embodiments the wake-up scheme employs an initial scan that uses a relatively wide frequency band. In this case the result of the initial scan may be used to determine whether to scan for signals using narrower frequency bands and/or to perform a full scan.

Figure 2:
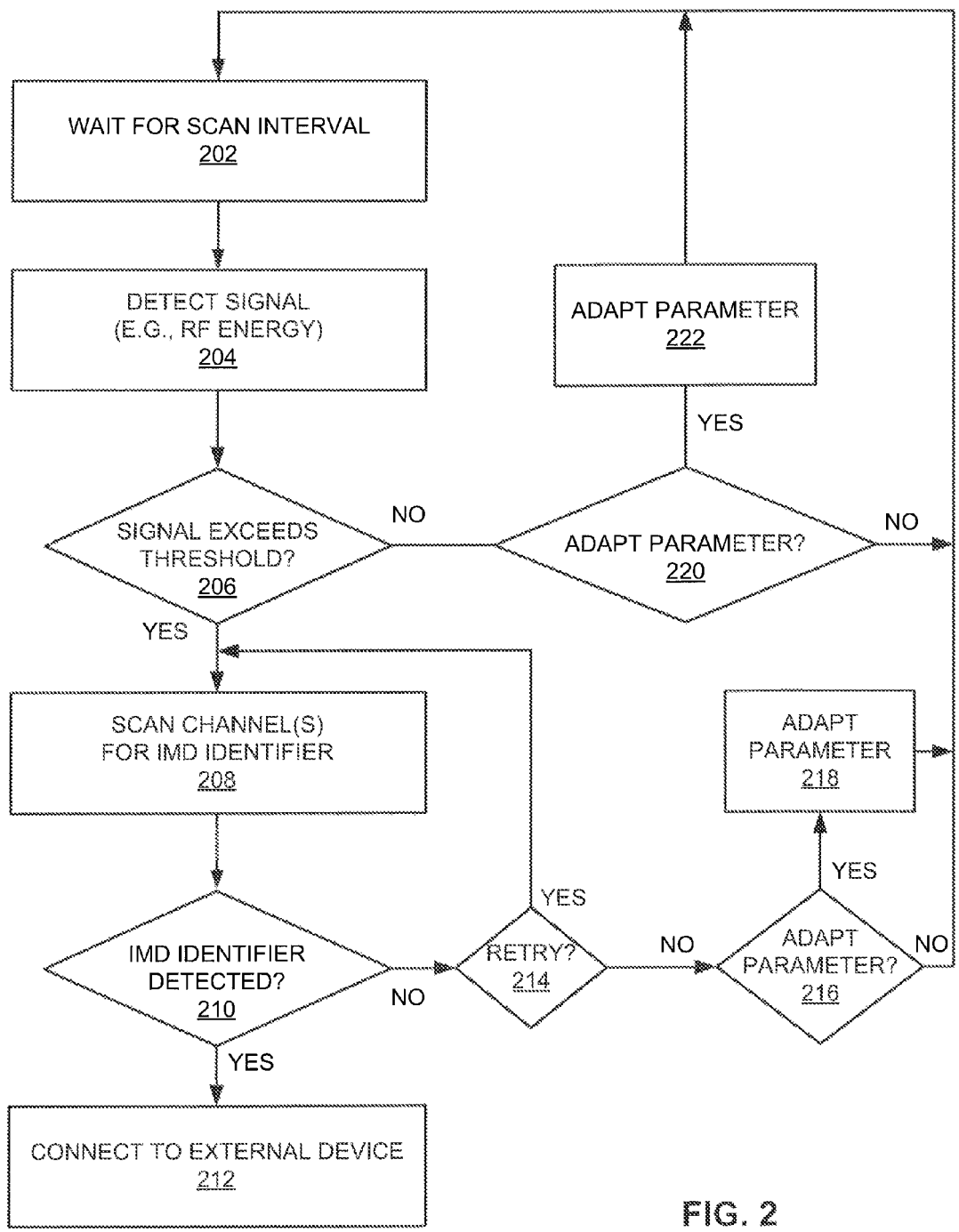
FIG. 2 is a flow chart of an embodiment of operations that may be performed to establish communication between an implantable medical device and an external device.
Figure 3:
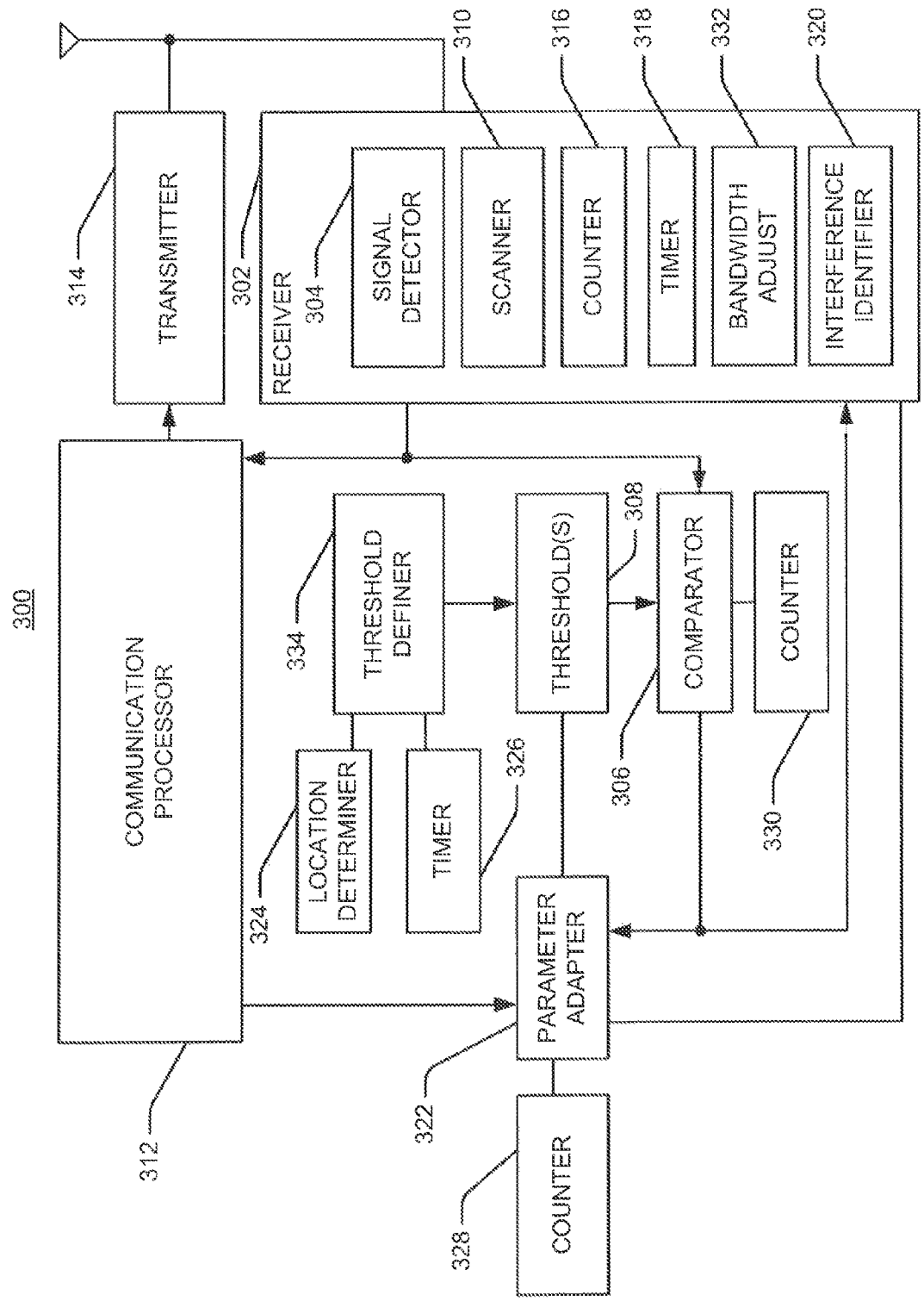
FIG. 3 is a simplified block diagram of an embodiment of a communication portion of an implantable medical device.
Figure 4:
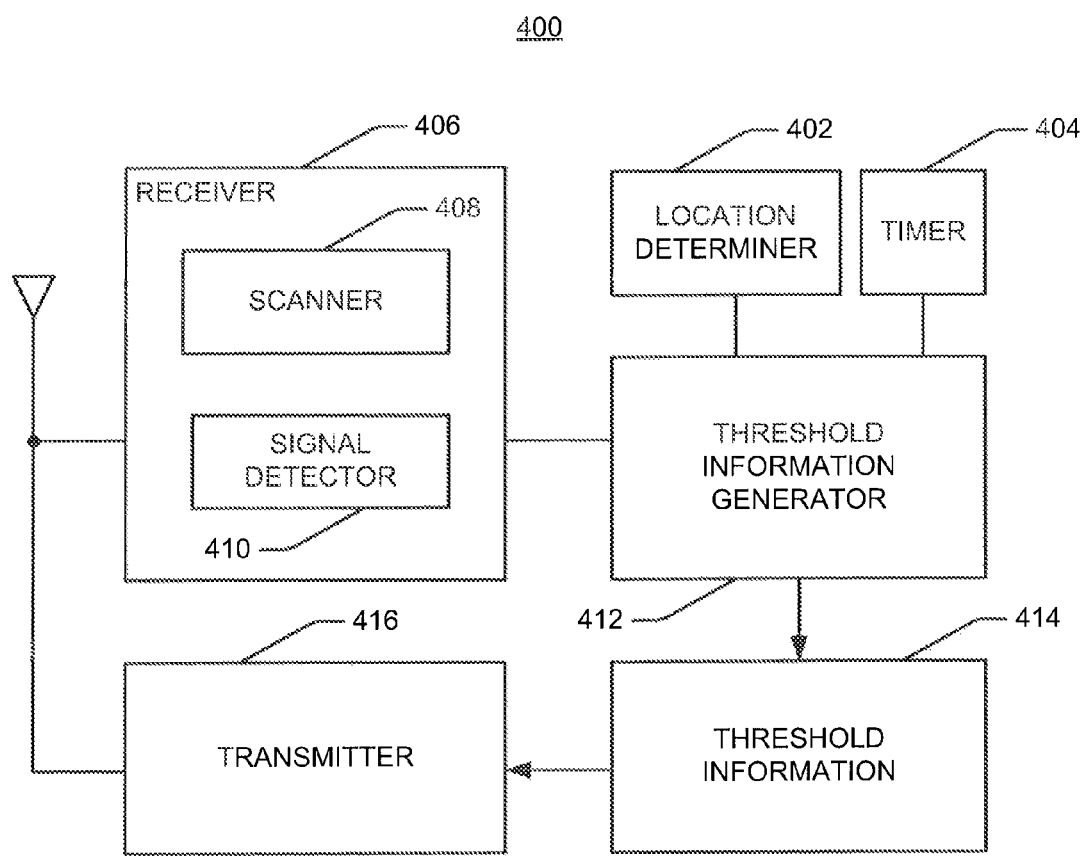
FIG. 4 is a simplified block diagram of an embodiment of a communication portion of an external device.

Additional details of an embodiment of an adaptive wake-up scheme will be discussed in more detail in conjunction with FIGS. 2, 3, and 4. FIG. 2 illustrates several sample operations that may be performed by an implantable medical device. FIG. 3 illustrates several sample components of an embodiment of an implantable medical device 300 (e.g., the device 102). FIG. 4 illustrates several sample components of an embodiment of an external device 400 (e.g., the device 104). For convenience, the operations of FIG. 2 (or any other operations discussed or taught herein) may be described as being performed by specific components (e.g., the devices 300 and 400). It should be appreciated, however, that these operations may be performed by other types of components and may be performed using a different number of components. It also should be appreciated that one or more of the operations described herein may not be employed in a given embodiment.

As represented by block 202 in FIG. 2, a receiver 302 of the device 300 may be periodically woken-up to determine whether the external device 400 is attempting to establish a communication session with the device 300. To this end, the receiver 302 may be configured in some embodiments to periodically scan (e.g., according to a defined scan interval) for signals within a given RF frequency band.

In some embodiments the devices 102 and 104 may communicate via one of several channels that are defined for a given frequency band. The use of multiple channels allows the devices 102 and 104 to elect to use a channel that provides the most effective communication medium (e.g., has the least amount of interference) at a given point in time. For example, in some embodiments the devices 102 and 104 may communicate via any of the channels defined for the medical implant communication service band. Hence, when the device 104 initially attempts to establish a communication session with the device 102, the device 104 selects a particular channel on which to transmit its request messages. In this case, the receiver 302 is configured to scan each of the channels of the designated communication band to determine whether the device 104 is currently sending messages over any of the channels.

As represented by block 204, the receiver 302 thus detects signals within a certain frequency range for a defined period of time. In some embodiments the operations of FIG. 2 may be performed separately for each channel. In other embodiments several channels (e.g., all of the channels) may be scanned together.

The signal detection of block 204 may advantageously be a relatively low power operation. Here, rather than scanning for a long period of time in an attempt to acquire an entire message transmitted by the device 104, the receiver 302 may scan for a short period of time (e.g., a few milliseconds) and utilize an appropriate mechanism (e.g., a signal detector component 304) to detect one or more attributes of any scanned signal. For example, the signal detector 304 may be configured to simply detect a magnitude, an energy level, frequency, phase, or some other attribute of a received signal. Hence, the operation of block 204 may involve partially "waking up" the device 300 since, for example, full operation of its communication components may not be needed at this point. In some embodiments the low-power, partially awakened mode may be invoked by enabling (e.g., powering on) only a portion of the communication components of the device 300 (e.g., component 302 and/or component 312). Also, the low-power, partially awakened mode may be invoked by modulating the duration for which one or more communication components are enabled (e.g., powered on). For example, the partially awakened mode may involve repeatedly enabling, over the course of a scan interval, one or more communication components for a relatively short period of time. In this case, power savings may thus be achieved by not turning on the component or components for the entire interval.

As represented by block 206 the device 300 may confirm whether the detected signal meets an adaptable criterion. Here, in some embodiments a comparator 306 compares the detected signal, if any, with one or more thresholds 308. For example, in some embodiments the amplitude of the detected signal may be compared with an amplitude-based threshold 308. Such a comparison may thus serve as a basis for determining whether to perform a more comprehensive scan.

Other types of comparisons or other suitable operations may be performed at block 206. For example, in some embodiments one or more frequency components of the detected signal may be analyzed or processed in some other manner (e.g., using frequency demodulation techniques) to provide an indication as to whether the detected signal may be associated with a signal from the external device. Also, in some embodiments the phase of the detected signal may be analyzed or processed in some other manner (e.g., using phase-locking techniques) to provide such an indication.

Accordingly, various types of characteristic-specific thresholds may be employed. For example, a threshold may relate to an amount of energy present in a signal, amplitude of a signal, frequency characteristics of a signal, phase of a signal, or some other suitable characteristic. Also, it should be appreciated that some embodiments may use a combination of two or more different types of thresholds.

In the event the selected property of the signal detected at block 204 equals or exceeds the threshold 308 at block 206 (or passes some other test with respect to the threshold), an assumption may be made that the signal may be from the device 104. Consequently, as represented by block 208 the device 300 may then elect to perform a comprehensive scan for signals from the device 400. Here, in response to an appropriate indication from the comparator 306, the receiver 302 (e.g. a scanner component 310) may scan one or more designated channels. In some embodiments, the channel or channels scanned at block 208 may be the same as those scanned at block 204. The scanner 310 may be adapted to scan each channel for a sufficiently long period of time to acquire any messages transmitted by the device 104. In addition, the scanner 310 may be adapted to analyze the received signals to extract any messages that are encoded in the signals. In particular, the scanner 310 may determine whether the message includes an identifier that identifies the implantable medical device ("IMD") 300. In this way, the scanner 310 may determine whether the device 400 has transmitted a signal to the device 300. To accomplish such a comprehensive (e.g., full) scan, the operation of block 208 may thus involve completing the "wake-up" discussed above to enable full operation of the communication components of the device 300. In some embodiments the higher-power, fully awakened mode may be invoked by enabling (e.g., powering on) all or substantially all of the communication components of the device 300 (e.g., component 302 and 312). In addition, in contrast with the partially awakened mode, the fully awakened mode may involve continually enabling one or more communication components over the course of an entire scan interval.

As represented by block 210, in the event the scanner 310 detects a message destined for the device 300 an appropriate indication may be provided to a communication processor 312 of the device 300. The communication processor 312 may then proceed to establish a connection with the device 400 by generating an appropriate response message and sending the message to the device 400 via a transmitter 314.

Referring again to block 210, operations that may be performed in the event the scanner 310 does not detect a message destined for the device 300 will now be discussed. In some embodiments, in response to a corresponding indication from the comparator 306, the scanner 310 may reattempt scanning for signals from the device 400 (block 214).

As represented by block 216, in the event the reattempts are not successful, one or more criteria may used to determine whether the threshold 308 or some other parameter (i.e., the adaptable criterion) used at block 206 should be adapted. Here, a determination may be made that the current detection test of block 206 is not selective enough (e.g., is too sensitive to detected signals) and is, as a result, causing an unacceptable number of scans to be performed at block 208 when the device 400 is not in fact transmitting signals to the device 300. For example, the presence of noise or in-band communication by other devices may result in a successful comparison at block 206 and, consequently, an unwanted transition to a high-level scan at block 208. To reduce the number of occurrences of such unwanted high-level scans, after a given number of failed searches a parameter employed at block 206 may be adapted. For example, the threshold 308 used at block 206 may be adapted to be less sensitive to noise or other signals within the frequency band of interest that are not from the device 400. Conversely, the amplification of receiver 302 could be increased, if a sufficient level of energy is not detected by comparator 306. Alternatively, in such case, the detection threshold 308 could be reduced.

Accordingly, in some embodiments the test of block 216 may be based on the number of scans at block 208, the number of successful determinations at block 210, or both. For example, parameter adaptation may be invoked if, for a given number of scans, a count of the number of unsuccessful scans exceeds a particular threshold or if a count of the number of successful scans falls below a particular threshold. To facilitate these counting operations, the receiver 302 may include a counter 316.

In some embodiments the test of block 216 may be based on one or more associated time periods. For example, parameter adaptation may be invoked if, over a certain time period, a count of the number of unsuccessful scans exceeds a particular threshold or if a count of the number of successful scans falls below a particular threshold. Also, the threshold 308 may be adapted if a connection has not been made (block 212) for a certain period of time. To facilitate these timing operations, the receiver 302 may include a timer 318.

In some embodiments the parameter adaptation decision may be based on the presence or absence of an interfering signal. For example, a threshold 308 may be increased (or some other parameter adapted) in an attempt to ensure that any interfering signals do not falsely trigger full scans. To this end, the device 300 may include an interference identifier 320 that may, for example, initiate one or more scans for interfering signals (e.g. relatively short, low-power scans) by the signal detector 304 or the scanner 310. To identify interference, the interference identifier 320 may compare the currently detected signal levels with a previously determined signal level baseline (e.g., a noise floor). Based on the results of this interference scan, the device 300 may determine whether a threshold 308 or some other parameter should be adapted due to an increase or a decrease in the magnitude of any interfering signals.

If the criterion or criteria of block 216 is/are not met, the operation flow may return to block 202 to wait for the next scan interval. In this case, the operations of FIG. 2 may simply be repeated (e.g., for the next channel or channels in the designated band, or for all of the channels).

Alternatively, in the event an adaptation criterion is met, an appropriate signal may be sent to a parameter adapter 322 (e.g., a threshold adapter) to initiate adaptation of the threshold or thresholds 308 or other parameter used at block 206. For example, at block 218 the parameter adapter 322 may increase the value of a threshold 308 so that a smaller number of the signal detections at block 204 will trigger a scan at block 208. Alternatively, the parameter adapter 322 may adjust amplification, filtering, or phase-related functionality of the receiver 302.

The parameter adapter 322 may take other information into account to adjust a threshold. For example, as discussed below the parameter adapter 322 may determine whether or how to adapt a threshold 308 based on baselines (e.g., noise floors) associated with various current conditions or based on information received from the apparatus 400. In the former case, the parameter adapter 322 may, as an example, increase the threshold 308 if the environment is particularly noisy. As an example of the latter case, the parameter adapter 322 may determine, based on information received from the device 400, that it is unlikely that there is any interference in a given channel.

As will be discussed in more detail below, in some embodiments the parameter adapter 322 may adapt the threshold 308 for a limited period of time. This type of parameter adaptation scheme may be used, for example, to compensate for any temporary interference in the channel being scanned.

In some embodiments several different thresholds 308 may be employed whereby one or more of these thresholds 308 may be adapted at block 218. For example, different threshold levels may be associated with different portions of the designated frequency band (e.g., different channels). In addition, different thresholds may be associated with amplitude, frequency, and phase of a detected signal. Thus, a given adaptation operation of block 218 may involve adapting one or more of these thresholds 308.

In addition, as will be discussed in more detail below, different thresholds 308 may be associated with different current conditions. Such conditions may include, for example, different locations, different times of day, different days of the week, month, or year, or some other criteria. In this case, the parameter adapter 322 may adjust the thresholds 308 based on information the device 300 collects regarding the corresponding current conditions. To this end, the device 300 may include a location determiner 324 that is adapted to determine the current location (e.g., based on global positioning system signals, or some other locating technique). In addition, the device 300 may include a timer 326 that is adapted to determine the current time of day, the current day, etc.

After the parameter adapter 322 adapts the threshold or thresholds 308 at block 218, the operation flow may return to block 202 to wait for the next scan interval. In this case, the operations of FIG. 2 may be repeated using the new threshold value or threshold values.

Referring back to block 206, in the event the comparison criteria is not met (e.g., the magnitude of any detected signal from block 204 is below the threshold 308 previously used at block 206), a determination may be made that the device 104 has not transmitted a signal. For example, in this case it may be determined or assumed that any detected signal is simply noise or interference. Conversely, it may be determined or assumed that the signal was generated by some other device (e.g., a similar external device located further away than the device 104).

As discussed above, in some embodiments the threshold 308 or some other parameter used at block 206 may be adaptable. In this case, a decision may be made at block 220 to adapt the threshold 308 or other parameter based on the latest detection of a signal that did not equal or exceed the threshold 308.

If at block 220 the threshold or thresholds 308, etc., is/are not to be adapted, the operation flow may return to block 202 to wait for the next scan interval. Again, the operations of FIG. 2 may then be repeated.

Conversely, if the threshold or thresholds 308, etc., is/are to be adapted, the operation flow proceeds to block 222. The adaptation decision of block 220 may be based on various criteria. For example, a decision may be made to lower the threshold 308 if relatively few of the recently detected signals have exceeded the threshold 308 at block 206.

To facilitate such adaptation, the apparatus 300 may include a counter 328 that counts, for example, the number of times a signal has exceeded the threshold 308 at block 206, the number of times a signal has not exceeded the threshold 308 at block 206, or both. In this case, the adaptation decision may be based on a comparison of the relative percentage of high magnitude versus low magnitude signals with a threshold 308. Similarly, the decision may be based on a comparison of the number of high magnitude or low magnitude signals with an appropriate threshold.

As discussed above, the threshold 308 may have been raised at a previous point in time (e.g., at block 218). If, since that time, a relatively low number of detected signals have exceeded the threshold 308 at block 206, a decision may be made to re-adapt the threshold 308. For example, the threshold 308 may be lowered to a prior threshold value. Similarly, if a level of amplification or some other parameter was adapted at block 218, the amplification or other parameter may be reset at block 222.

In some embodiments the adaptation decision may be based on a defined amount of time. For example, the parameter adapter 322 may lower the threshold 308 if relatively few detected signals have exceeded the threshold 308 at block 206 over a certain period of time. In these embodiments, the timer 326 may be used to calculate any pertinent time periods.

In some embodiments the threshold 308 or other parameter may be adapted automatically based on the amount of time that has passed since the threshold 308 was raised. For example, the parameter adapter 322 may adapt (e.g., increase) the threshold 308 for a designated period of time (e.g., as discussed above in conjunction with block 218). In this case, once the designated period of time elapses, the parameter adapter 322 may automatically reset the threshold 308 to a prior threshold value.

As discussed above the parameter adapter 322 also may adapt the threshold 308 or other parameter based on the current location of the device 300 or based on the presence or absence of an interfering signal. Thus, the location determiner 324 may check the location of the device 300 at block 220 to determine whether the threshold 308 should be adapted due to a change in location. In addition, the interference identifier 320 may initiate a scan for interfering signals to determine whether the threshold 308, or the amplification of receiver 302, should be adapted due to an increase or a decrease in the magnitude of any interfering signals.

After the parameter adapter 322 adapts the threshold or thresholds 308 or other parameter at block 222, the operation flow may return to block 202 to wait for the next scan interval.

In this case, the operations of FIG. 2 may be repeated using the new threshold value or threshold values.

It should be appreciated that the operations described above may be modified in various ways. In some embodiments the results of several lower-level scans may be used to determine whether to invoke the high-level scan of block 208.

For example, in some embodiments the comparator 306 may send a comparison result to the receiver 302 only after several signals have been sampled at block 204 and each of these samples have been compared to one or more thresholds 308 at block 206. In this case, the device 300 may include a counter 330 for counting the number of successful threshold tests, the number of unsuccessful threshold tests, or both, for determining whether an acceptable number of successful comparisons have been made at block 206.

In addition, some embodiments may employ several levels of lower-level scans that are used to determine whether to invoke the high-level scan of block 208. For example, rather than proceeding to block 208 after a successful comparison at block 206, the operation flow may return back to block 204 to perform another scan. In some embodiments, the additional scan may comprise a more comprehensive scan and an associated comparison. This process may then be repeated for each lower level that is defined for a particular application. Here, the scans for the different levels may use different scanning parameters (e.g., a longer scan time, different frequency filters, different phase parameters, and different thresholds 308). If all of the lower-level scans meet their respective threshold criteria, the full scan of block 208 may then be invoked.

The embodiments above presented solutions that involve in some aspects threshold detection techniques. Without departing from the spirit of the teachings herein, one skilled in the art could employ other techniques with equivalent or similar results. For example, frequency modulation/demodulation schemes or phased-locked loop techniques may be effectively employed in conjunction with a wake-up scheme. With such approach, rather than adapting the detection threshold or the amplification of the receiver, one could adjust the gain of the phased-lock loop or its filter parameters. Alternatively, other characteristics of the received signal could be used in the energy 'sniff' process. The detection thresholds of block 308 would then be specific and in accordance to the particular signal characteristics used in the process.

Figure 5:
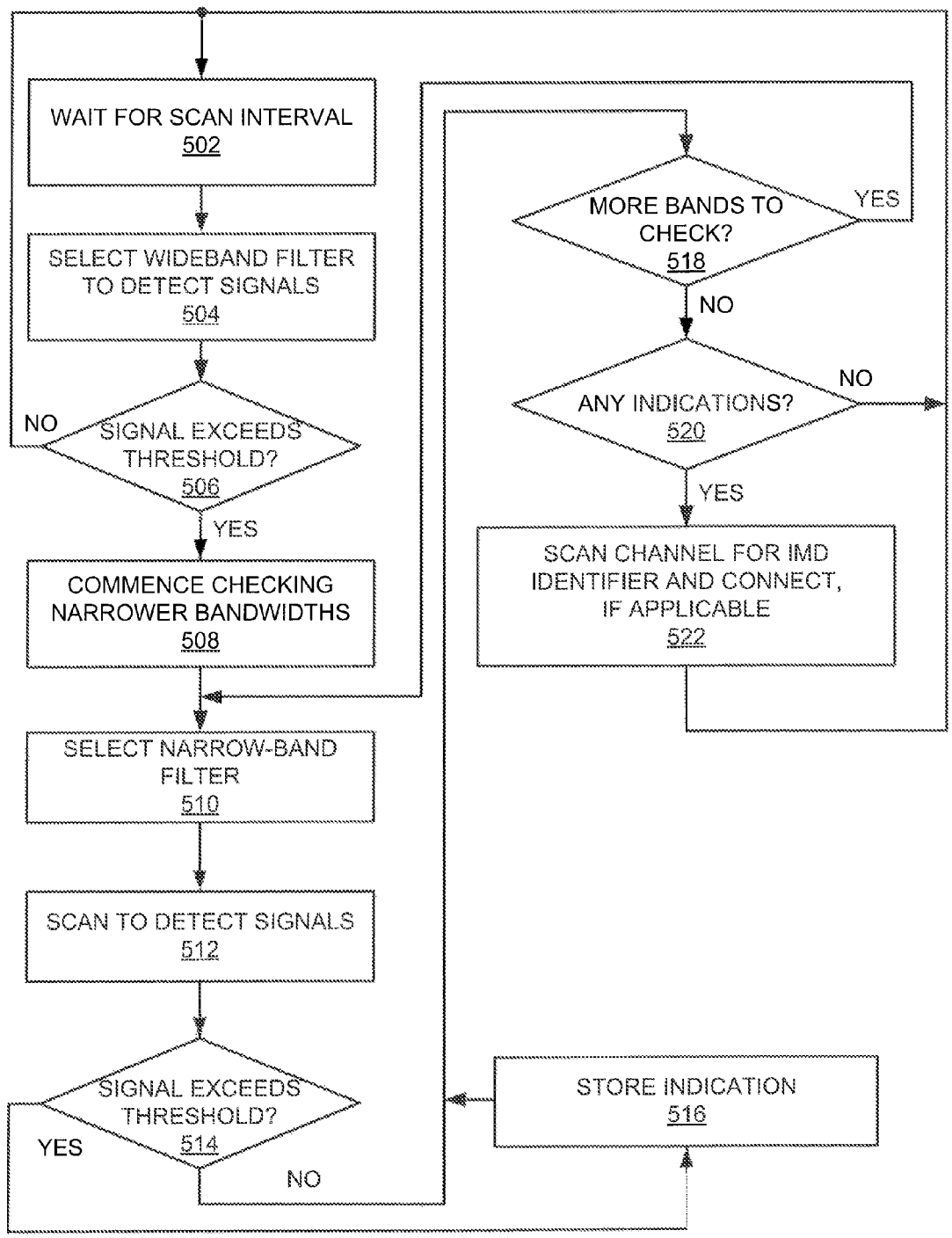
FIG. 5 is a flow chart of an embodiment of operations that may be performed to establish communication between an implantable medical device and an external device.

In some embodiments an initial scan may be made over a relatively wide frequency band and subsequent scans made over narrower frequency bands. FIG. 5 illustrates several sample operations that may be performed in an embodiment that employs such a variable bandwidth scheme.

As represented by block 502, the receiver 302 is periodically woken-up to perform a scan. This operation may be similar to the operation discussed above in conjunction with block 202.

As represented by block 504, a bandwidth adjust component 332 of the receiver 302 selects an initial frequency band to scan. Here, the receiver 302 may initially be configured to scan over a relative wide frequency range. For example, a selected range may cover all of the channels within which the external device may transmit signals. To this end, the bandwidth adjust component 332 may configure the receiver 302 to use a wideband filter for this scan. In some embodiments the scan of block 504 may be a relatively lower power scan (e.g., as in block 204).

At block 506, a signal detected at block 506 is compared to one or more thresholds 308. In a similar manner as discussed above, if the test is not met (e.g., the amplitude of a signal is less than a threshold 308), the process may return to block 502 for the next scan.

In contrast, if a sufficient level of energy is detected during the initial scan, the device 300 may then perform one or more scans over narrower frequency ranges starting at block 508. For example, these subsequent scans may be conducted over certain subsets of the channels scanned at block 504.

As represented by block 510 the bandwidth adjust component 332 selects a narrower band to be used for the second level of the variable-bandwidth wake-up scheme. This may involve, for example, selecting a narrow-band filter to be used during the scan.

As represented by block 512 the receiver 302 performs the narrower scan to detect any signals that may exist within the prescribed frequency range. As mentioned above, this scan may be performed on a first subset of the channels scanned at block 504. In addition, each scan performed at block 512 may be a relatively lower power scan as compared to a full scan. In some embodiments, however, each subsequently higher-level scan may involve a longer signal lock, thereby resulting in more power consumption than the scans at a prior level.

At block 514, the detected signal, if any, is compared with an appropriate threshold 308. In some embodiments a corresponding indication is stored in the event the detected narrower band signal equals or exceeds the threshold 308 at block 514.

In either case, the operation flow proceeds to block 518 where it is determined whether any more frequency ranges need to be checked at this level. If so, the operation flow returns to block 510 to commence scanning, for example, the next subset of the channels scanned at block 504.

At block 520, if none of the scans at the second level exceeded the corresponding threshold 308, the operation flow returns to block 502. If, on the other hand, at least one of the scans did result in a successful threshold comparison at block 514, the receiver 302 may be configured to perform a full scan to determine whether the device 400 has sent a message to the device 300. These operations may be similar to the operations of blocks 208-212 discussed above. In some embodiments the scan of block 522 may be performed over the frequency band or bands (e.g., channel or channels) identified at block 520.

In some embodiments the multi-band scanning technique of FIG. 5 may employ several levels of scans. As an example an initial scan at block 504 may cover eight channels (e.g. channels 1-8). The scans at a subsequent level may consist of two scans of four channels each (e.g., channel 1-4 and channels 4-8). Assuming that only the scan of channels 1-4 resulted in a successful threshold comparison at block 514, the next scan may consist of two scans of two channels each(e.g., channel 1-2 and channels 3-4). Operations such as these may then be repeated until a channel or channels are identified for conducting a full scan.

In some embodiments one or more of the stages may be bypassed. For example, the algorithm may be adapted to skip any testing of additional bands once a signal has been detected in a given band. In this way, a given search may be performed more quickly and may consume less power. Alternatively, if a signal of a sufficient magnitude is detected in the wideband search (e.g., block 504) the device 300 may proceed directly to a full scan on each channel at block 522.

In some embodiments the multi-band scanning technique of FIG. 5 maybe used in conjunction with the adaptive threshold technique of FIG. 2. For example, the thresholds 308 used in blocks 506 and 514 may be adapted in a similar manner as discussed above to reduce the number of times a full scan does not result in a connection with the device 400. In addition, different thresholds may be employed for the different levels and thresholds may be adjusted based on the success or failure of a comparison or a scan (e.g., a high level scan) at each level. Similarly, the different scan levels of FIG. 2 may employ successively different frequency bands using some of the techniques of FIG. 5.

As mentioned above, the teachings herein are not limited to amplitude-base threshold detections techniques. Other signal characteristics could be used with similar results.

Also, in some embodiments other parameters may be adapted to improve the accuracy with which the low-level scans predict that the device 400 is transmitting a message to the device 300, or to improve the operation of the wake-up scheme in some other manner. For example, the apparatus 300 may change the duration of the scan interval to cause the low-level scan to be performed less frequently or more frequently based on the success or failure of a comparison or a scan at one or more levels. In addition, in some embodiments the dwell time for the full scan may be adapted based on the successes or failures at block 210 (e.g. over a recent time period) to provide an acceptable tradeoff between accurately detecting messages from the apparatus 400 and saving power.

Based on the above it should be appreciated that the teachings herein may be advantageously employed to reduce the power consumed by the device 300 in conjunction with scanning for signals and/or may improve the corresponding response time of the wake-up scheme. For example, by using initial scanning levels that consume less power, the frequency with which the apparatus 300 performs a full scan may be reduced. Consequently, the power consumption of the device 300 may be reduced. In addition, in some embodiments the scan interval may be decreased to provide a faster device wake-up and connection time (e.g., on the order of 30 seconds or less). For example, since the initial scans consume less power, they may be performed more frequently without significantly impacting the power consumption of the device 300. Consequently, adaptation may be employed to optimize (e.g., reduce) a wake-up time of the device.

Moreover, through the use of the adaptation techniques taught herein, the probability of missed or false detections may be reduced. This may be achieved, for example, by adapting (e.g., adapting the thresholds 308) to the RF environment as discussed herein.

Also, adaptation may be employed to optimize (e.g., increase) a communication range of the device 300. For example, relatively long-range communication channels may be established (e.g., on the order of 15 feet or more) through the use of a frequency band such as a medical implant communication service band in the 402-405 MHz range (or any future extension of that range, e.g., 401-406 MHz). Here, any additional power that may be used to operate at these frequencies and distances may be offset by the power reduction that may be achieved as mentioned above.

Furthermore the wake-up scheme may be completely automated. That is, no intervention on the part of the patient may be needed to enable the device 300 to communicate with the device 400.

Moreover, the teachings herein may be advantageously employed without synchronizing the communication times between the devices 300 and 400. For example, as discussed above the device 300 may automatically scan for signals from the device 400 at relatively frequent intervals. In this way, any attempt by the device 400 to establish communication may be responded to in a relatively short period of time. Consequently, problems associated with trying to maintain synchronization between the devices or recovering from a loss of synchronization may be avoided.

In some embodiments at least a portion of the functionality described herein may be reversed between the devices 300 and 400. For example, in an emergency situation (or some other suitable situation) the device 300 may unilaterally transmit a signal to the device 400 (e.g., a wearable monitor). In this case, the wearable monitor may employ a wake-up scheme as taught herein to periodically listen for signals from the device 300.

In some embodiments the device 300, the device 400, or both of the devices 300 and 400 working in cooperation, may define the parameters (e.g., the thresholds 308, an amplification level, etc.) for the wake-up scheme based on one or more conditions. Several sample operations relating to defining such parameters will now be treated in conjunction with FIGS. 6 and 7. For convenience, the following describes an example where threshold related-information is defined. It should be appreciated, however, that these concepts may be applicable to other types of parameters as well.

Figure 6:
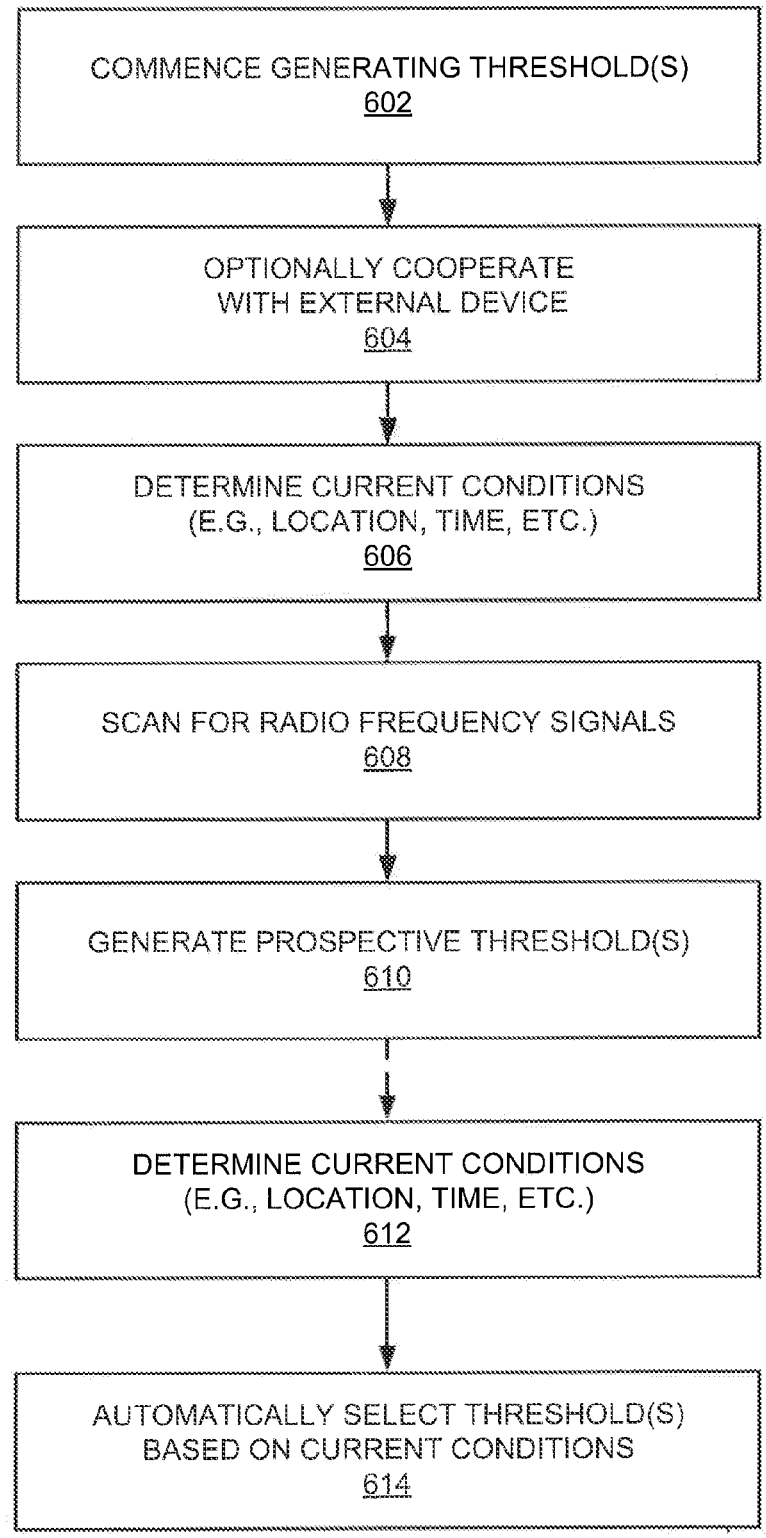
FIG. 6 is a flow chart of an embodiment of operations that may be performed to define one or more detection-related parameters.

FIG. 6 describes several operations that may be performed by an implantable medical device (e.g., the device 300) to define and select one or more thresholds 308. Here, blocks 602-610 relate to operations that may be used to define thresholds 308 that are associated with particular conditions. In addition, blocks 612 and 614 relate to operations that may be performed to select a particular threshold 308 based on current conditions.

The threshold generation process commences at block 602. This process may be performed, for example, by a threshold definer 334 (FIG. 3) on a recurring basis, or based on some stimulus or the occurrence of some event. For example the operations of blocks 602-610 may be invoked when the device 300 is powered-on, at regular intervals, when movement of the patient is detected, or at some other point in time.

As represented by block 604 the device 300 may optionally cooperate with the device 400 to generate the threshold or thresholds 308. For example, in some embodiments the devices 300 and 400 may select one or more time periods during which the device 400 will not transmit any signals. In this way, the device 300 may monitor ambient signals at the designated time or times to define an RF signal noise floor that represents, for example, a minimum level for the threshold 308.

Alternatively, as will be discussed in more detail below in conjunction with FIG. 7, the device 400 may monitor ambient signals to generate threshold information. In this case, the device 300 may receive this information from the device 400 at block 604 or at some other time.

At block 606 the device 300 may determine one or more current conditions. As discussed above, these conditions may include the current location, the current time, the current day, and so on.

The device 300 may then scan the designated frequency band or bands at block 608. Here, the device 300 may measure the ambient signals for each channel under the defined conditions.

At block 610 the device 300 defines (e.g., generates) one or more thresholds 308 associated with the current conditions. In addition, the operations of blocks 602-610 may be repeated to define thresholds 308 associated with one or more other conditions (e.g., different locations, different times, etc.).

Referring now to the operations of blocks 612 and 614, at some point in time the device 300 may adapt the threshold 308 currently being used. Such an operation may relate to, for example, the operations of blocks 218 and 222 discussed above. Accordingly, the device 300 may determine the current conditions and automatically adapt the current threshold 308 based on the threshold information associated with these same conditions or similar conditions (block 614).

In some embodiments the threshold information derived by the device 300 may be uploaded to the device 400. The device 400 may thereby collect this information from multiple implanted devices 300 (e.g., from multiple patients) and use this collective information to further improve the initial definitions of the thresholds 308 and the adaptations of the thresholds 308.

As mentioned above, the teachings herein are not limited to amplitude-base threshold detections techniques. Other signal characteristics could be used with similar results.

Figure 7:
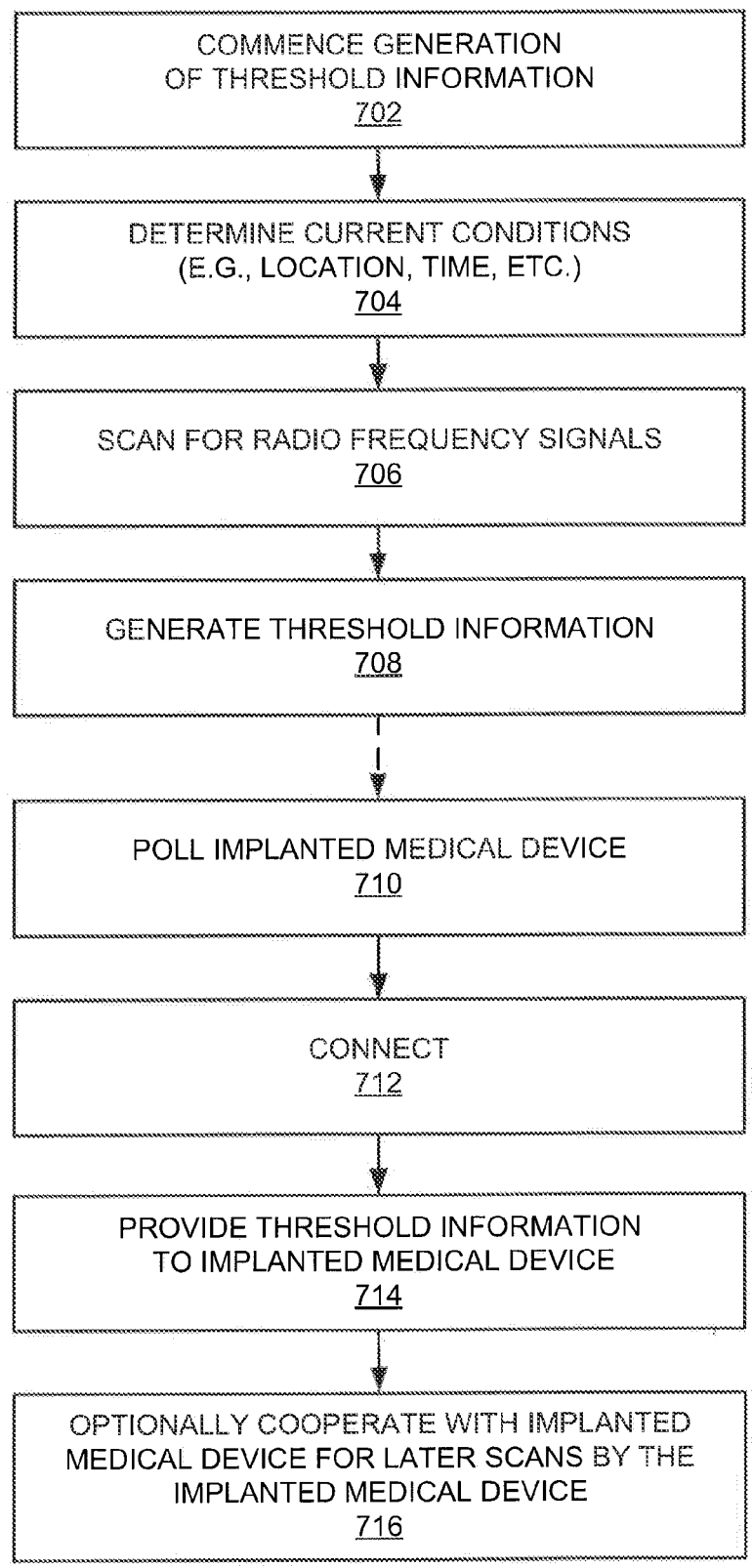
FIG. 7 is a flow chart of an embodiment of operations that may be performed to generate detection-related parameter information.

Referring now to FIG. 7, several operations that may be performed by an external device (e.g., the device 400) to define information associated with one or more thresholds 308 will now be discussed. Blocks 702-708 relate to operations for generating threshold-related information that is associated with certain conditions. Blocks 710-716 relate to operations for communicating with an implantable medical device (e.g., device 300) and providing the threshold-related information to the implantable medical device.

The threshold information generation process commences at block 702. In a similar manner as discussed above, this process may be performed, for example, on a recurring basis, or based on some form of stimulus or the occurrence of some event. For example the operations of blocks 702-708 may be invoked when the device 400 is powered-on, at regular intervals, when invoked by user input, or at some other point in time.

At block 704 the device 400 may determine one or more current conditions. As discussed above, these conditions may include the current location, the current time, the current day, and so on. The device 400 may thus include a location determiner 402 and a timer 404 that may be similar to the corresponding components described above in conjunction with FIG. 3.

A receiver 406 of the device 400 may then scan the designated frequency band or bands at block 706. In a similar manner as discussed above, the device 400 may measure the ambient signals for each channel and under the certain conditions. In particular, the device 400 may monitor the ambient signals to define an RF signal noise floor that relates to, for example, a minimum level for the threshold 308. In some embodiments the receiver may employ a scanner component 408 for performing the scanner operations. In addition, or in the alternative, the device 400 may include a signal detector 410 that is similar to the signal detector 204 of FIG. 2 whereby the signal detectors 204 and 410 may generate similar signal information.

At block 708 a threshold information generator 412 of the device 400 defines (e.g., generates) threshold information 414 associated with the current conditions. In some embodiments this information may comprise the actual thresholds 308 used by the device 300. In other embodiments this information may comprise information that the device 300 uses to define or use the thresholds 308. For example, based on its monitoring operations over time, the device 400 may inform the device 300 that it is unlikely to see any interference in a certain channel or certain channels. The operations of blocks 702-708 may then be repeated to define thresholds 308 associated with one or more other conditions (e.g., different locations, different times, etc.).

Referring now to the operations of blocks 710-716, at some point in time the device 400 may establish a communication session with the device 300. As discussed above, this process may involve a transmitter 416 of the device 400 sending a polling message (e.g., a request message) to the device 300 (block 710) and subsequently establishing a connection in the event the device 300 properly responds to the polling message (block 712).

As represented by blocks 714 and 716, at some point the device 400 may cooperate with the device 300 to define threshold information to be used by the device 300 (e.g., as discussed above in conjunction with block 604). For example, the transmitter 416 may send the threshold information 414 to the device 300 (block 714). In addition, the device 400 may select one or more time periods during which it will not transmit any signals (block 716).

As mentioned above, the teachings herein are not limited to amplitude-base threshold detections techniques. Other signal characteristics could be used with similar results.

Exemplary Cardiac Device

As mentioned above, the teachings herein may be utilized in conjunction with an implantable cardiac device. The following describes an example of an implantable cardiac device (e.g., a stimulation device such as an implantable cardioverter defibrillator, a pacemaker, etc.) that is capable of being used in connection with the various embodiments that are described herein. It is to be appreciated and understood that other cardiac devices, including those that are not necessarily implantable, can be used and that the description below is given, in its specific context, to assist the reader in understanding, with more clarity, the embodiments described herein.

Figure 8:
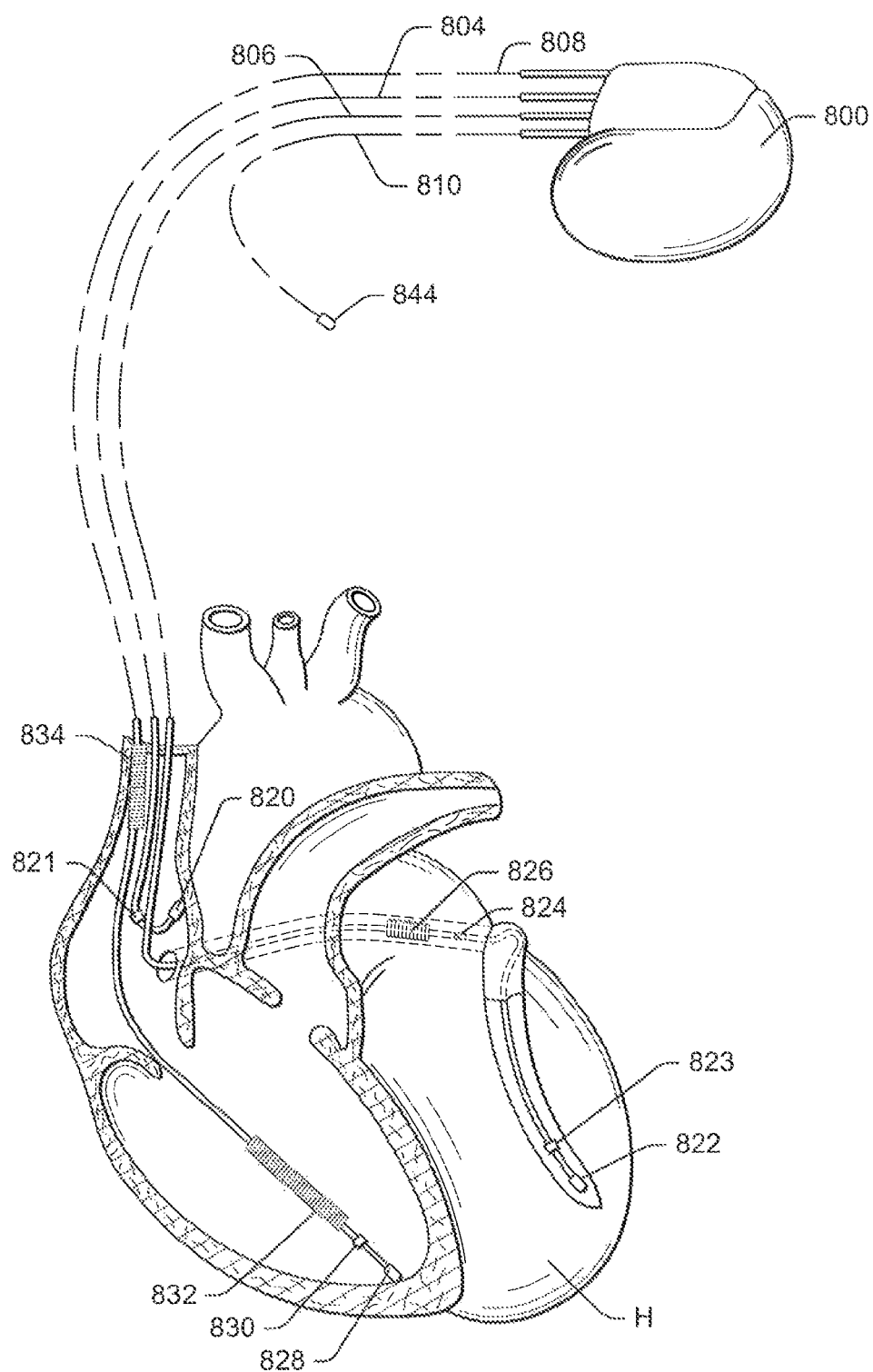
FIG. 8 is a simplified diagram of an embodiment of an implantable stimulation device in electrical communication with one or more leads implanted in a patient's heart for sensing conditions in the patient, delivering therapy to the patient, or providing some combination thereof.

FIG. 8 shows an exemplary implantable cardiac device 800 in electrical communication with a patient's heart H by way of three leads 804, 806, and 808, suitable for delivering multi-chamber stimulation and shock therapy. To sense atrial cardiac signals and to provide right atrial chamber stimulation therapy, the device 800 is coupled to an implantable right atrial lead 804 having, for example, an atrial tip electrode 820, which typically is implanted in the patient's right atrial appendage or septum. FIG. 8 also shows the right atrial lead 804 as having an optional atrial ring electrode 821.

To sense left atrial and ventricular cardiac signals and to provide left chamber pacing therapy, the device 800 is coupled to a coronary sinus lead 806 designed for placement in the coronary sinus region via the coronary sinus for positioning one or more electrodes adjacent to the left ventricle, one or more electrodes adjacent to the left atrium, or both. As used herein, the phrase "coronary sinus region" refers to the vasculature of the left ventricle, including any portion of the coronary sinus, the great cardiac vein, the left marginal vein, the left posterior ventricular vein, the middle cardiac vein, the small cardiac vein or any other cardiac vein accessible by the coronary sinus.

Accordingly, an exemplary coronary sinus lead 806 is designed to receive atrial and ventricular cardiac signals and to deliver left ventricular pacing therapy using, for example, a left ventricular tip electrode 822 and, optionally, a left ventricular ring electrode 823; provide left atrial pacing therapy using, for example, a left atrial ring electrode 824; and provide shocking therapy using, for example, a left atrial coil electrode 826 (or other electrode capable of delivering a shock). For a more detailed description of a coronary sinus lead, the reader is directed to U.S. Pat. No. 5,466,254, "Coronary Sinus Lead with Atrial Sensing Capability" (Holland), which is incorporated herein by reference.

The device 800 is also shown in electrical communication with the patient's heart H by way of an implantable right ventricular lead 808 having, in this embodiment, a right ventricular tip electrode 828, a right ventricular ring electrode 830, a right ventricular (RV) coil electrode 832 (or other electrode capable of delivering a shock), and a superior vena cava (SVC) coil electrode 834 (or other electrode capable of delivering a shock). Typically, the right ventricular lead 808 is transvenously inserted into the heart H to place the right ventricular tip electrode 828 in the right ventricular apex so that the RV coil electrode 832 will be positioned in the right ventricle and the SVC coil electrode 834 will be positioned in the superior vena cava. Accordingly, the right ventricular lead 808 is capable of sensing or receiving cardiac signals, and delivering stimulation in the form of pacing and shock therapy to the right ventricle.

The device 800 is also shown in electrical communication with a lead 810 including one or more components 844 such as a physiologic sensor. The component 844 may be positioned in, near or remote from the heart.

It should be appreciated that the device 800 may connect to leads other than those specifically shown. In addition, the leads connected to the device 800 may include components other than those specifically shown. For example, a lead may include other types of electrodes, sensors or devices that serve to otherwise interact with a patient or the surroundings.

Figure 9:
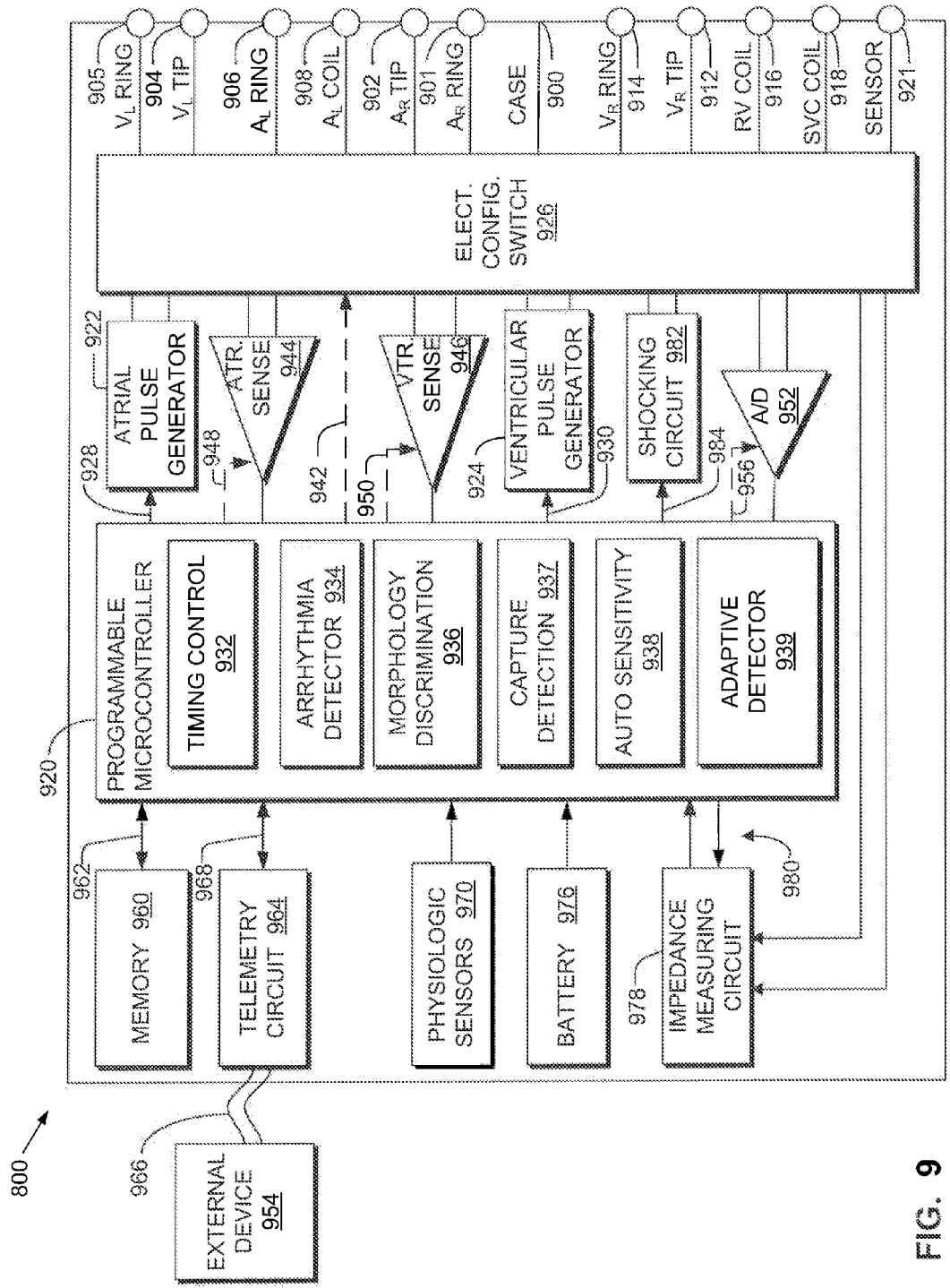
FIG. 9 is a simplified functional block diagram of an embodiment of an implantable cardiac device, illustrating basic elements that may be configured to sense conditions in the patient, deliver therapy to the patient, or provide some combination thereof.

FIG. 9 depicts an exemplary, simplified block diagram illustrating sample components of the device 800. The device 800 may be adapted to treat both fast and slow arrhythmias with stimulation therapy, including cardioversion, defibrillation, and pacing stimulation. While a particular multi-chamber device is shown, it is to be appreciated and understood that this is done for illustration purposes. Thus, the techniques and methods described below can be implemented in connection with any suitably configured or configurable device. Accordingly, one of skill in the art could readily duplicate, eliminate, or disable the appropriate circuitry in any desired combination to provide a device capable of treating the appropriate chamber(s) with, for example, cardioversion, defibrillation, and pacing stimulation.

Housing 900 for the device 800 is often referred to as the "can", "case" or "case electrode", and may be programmably selected to act as the return electrode for all "unipolar" modes. The housing 900 may further be used as a return electrode alone or in combination with one or more of the coil electrodes 826, 832 and 834 for shocking purposes. Housing 900 further includes a connector (not shown) having a plurality of terminals 901, 902, 904, 905, 906, 908, 912, 914, 916, and 918 (shown schematically and, for convenience, the names of the electrodes to which they are connected are shown next to the terminals). The connector may be configured to include various other terminals depending on the requirements of a given application. For example, a terminal 921 may connect to one or more sensors located external to the device 800.

To achieve right atrial sensing and pacing, the connector includes, for example, a right atrial tip terminal (AR TIP) 902 adapted for connection to the right atrial tip electrode 820. A right atrial ring terminal (AR RING) 901 may also be included and adapted for connection to the right atrial ring electrode 821. To achieve left chamber sensing, pacing, and shocking, the connector includes, for example, a left ventricular tip terminal (VL TIP) 904, a left ventricular ring terminal (VL RING) 905, a left atrial ring terminal (AL RING) 906, and a left atrial shocking terminal (AL COIL) 908, which are adapted for connection to the left ventricular tip electrode 822, the left ventricular ring electrode 823, the left atrial ring electrode 824, and the left atrial coil electrode 826, respectively.

To support right chamber sensing, pacing, and shocking, the connector further includes a right ventricular tip terminal (VR TIP) 912, a right ventricular ring terminal (VR RING) 914, a right ventricular shocking terminal (RV COIL) 916, and a superior vena cava shocking terminal (SVC COIL) 918, which are adapted for connection to the right ventricular tip electrode 828, the right ventricular ring electrode 830, the RV coil electrode 832, and the SVC coil electrode 834, respectively.

At the core of the device 800 is a programmable microcontroller 920 that controls the various modes of stimulation therapy. As is well known in the art, microcontroller 920 typically includes a microprocessor, or equivalent control circuitry, designed specifically for controlling the delivery of stimulation therapy, and may further include memory such as RAM, ROM and flash memory, logic and timing circuitry, state machine circuitry, and I/O circuitry. Typically, microcontroller 920 includes the ability to process or monitor input signals (data or information) as controlled by a program code stored in a designated block of memory. The type of microcontroller is not critical to the described embodiments. Rather, any suitable microcontroller 920 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Thornander et al.) and U.S. Pat. No. 4,944,298 (Sholder), all of which are incorporated by reference herein. For a more detailed description of the various timing intervals that may be used within the device and their inter-relationship, see U.S. Pat. No. 4,788,980 (Mann et al.), also incorporated herein by reference.

FIG. 9 also shows an atrial pulse generator 922 and a ventricular pulse generator 924 that generate pacing stimulation pulses for delivery by the right atrial lead 804, the coronary sinus lead 806, the right ventricular lead 808, or some combination of these leads via an electrode configuration switch 926. It is understood that in order to provide stimulation therapy in each of the four chambers of the heart, the atrial and ventricular pulse generators 922 and 924 may include dedicated, independent pulse generators, multiplexed pulse generators, or shared pulse generators. The pulse generators 922 and 924 are controlled by the microcontroller 920 via appropriate control signals 928 and 930, respectively, to trigger or inhibit the stimulation pulses.

Microcontroller 920 further includes timing control circuitry 932 to control the timing of the stimulation pulses (e.g., pacing rate, atrioventricular (A-V) delay, atrial interconduction (A-A) delay, or ventricular interconduction (V-V) delay, etc.) or other operations, as well as to keep track of the timing of refractory periods, blanking intervals, noise detection windows, evoked response windows, alert intervals, marker channel timing, etc., as known in the art.

Microcontroller 920 further includes an arrhythmia detector 934. The arrhythmia detector 934 may be utilized by the device 800 for determining desirable times to administer various therapies. The arrhythmia detector 934 may be implemented, for example, in hardware as part of the microcontroller 920, or as software/firmware instructions programmed into the device 800 and executed on the microcontroller 920 during certain modes of operation.

Microcontroller 920 may include a morphology discrimination module 936, a capture detection module 937 and an auto sensing module 938. These modules are optionally used to implement various exemplary recognition algorithms or methods. The aforementioned components may be implemented, for example, in hardware as part of the microcontroller 920, or as software/firmware instructions programmed into the device 800 and executed on the microcontroller 920 during certain modes of operation.

The electrode configuration switch 926 includes a plurality of switches for connecting the desired terminals (e.g., that are connected to electrodes, coils, sensors, etc.) to the appropriate I/O circuits, thereby providing complete terminal and, hence, electrode programmability. Accordingly, switch 926, in response to a control signal 942 from the microcontroller 920, may be used to determine the polarity of the stimulation pulses (e.g., unipolar, bipolar, combipolar, etc) by selectively closing the appropriate combination of switches (not shown) as is known in the art.

Atrial sensing circuits (ATR. SENSE) 944 and ventricular sensing circuits (VTR. SENSE) 946 may also be selectively coupled to the right atrial lead 804, coronary sinus lead 806, and the right ventricular lead 808, through the switch 926 for detecting the presence of cardiac activity in each of the four chambers of the heart. Accordingly, the atrial and ventricular sensing circuits 944 and 946 may include dedicated sense amplifiers, multiplexed amplifiers, or shared amplifiers. Switch 926 determines the "sensing polarity" of the cardiac signal by selectively closing the appropriate switches, as is also known in the art. In this way, the clinician may program the sensing polarity independent of the stimulation polarity. The sensing circuits (e.g., circuits 944 and 946) are optionally capable of obtaining information indicative of tissue capture.

Each sensing circuit 944 and 946 preferably employs one or more low power, precision amplifiers with programmable gain, automatic gain control, bandpass filtering, a threshold detection circuit, or some combination of these components, to selectively sense the cardiac signal of interest. The automatic gain control enables the device 800 to deal effectively with the difficult problem of sensing the low amplitude signal characteristics of atrial or ventricular fibrillation.

The outputs of the atrial and ventricular sensing circuits 944 and 946 are connected to the microcontroller 920, which, in turn, is able to trigger or inhibit the atrial and ventricular pulse generators 922 and 924, respectively, in a demand fashion in response to the absence or presence of cardiac activity in the appropriate chambers of the heart. Furthermore, as described herein, the microcontroller 920 is also capable of analyzing information output from the sensing circuits 944 and 946, a data acquisition system 952, or both. This information may be used to determine or detect whether and to what degree tissue capture has occurred and to program a pulse, or pulses, in response to such determinations. The sensing circuits 944 and 946, in turn, receive control signals over signal lines 948 and 950, respectively, from the microcontroller 920 for purposes of controlling the gain, threshold, polarization charge removal circuitry (not shown), and the timing of any blocking circuitry (not shown) coupled to the inputs of the sensing circuits 944 and 946 as is known in the art.

For arrhythmia detection, the device 800 utilizes the atrial and ventricular sensing circuits 944 and 946 to sense cardiac signals to determine whether a rhythm is physiologic or pathologic. It should be appreciated that other components may be used to detect arrhythmia depending on the system objectives. In reference to arrhythmias, as used herein, "sensing" is reserved for the noting of an electrical signal or obtaining data (information), and "detection" is the processing (analysis) of these sensed signals and noting the presence of an arrhythmia.

Timing intervals between sensed events (e.g., P-waves, R-waves, and depolarization signals associated with fibrillation) may be classified by the arrhythmia detector 934 of the microcontroller 920 by comparing them to a predefined rate zone limit (e.g., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy"). Similar rules may be applied to the atrial channel to determine if there is an atrial tachyarrhythmia or atrial fibrillation with appropriate classification and intervention.

Cardiac signals or other signals may be applied to inputs of an analog-to-digital (A/D) data acquisition system 952. The data acquisition system 952 is configured (e.g., via signal line 956) to acquire intracardiac electrogram ("IEGM") signals or other signals, convert the raw analog data into a digital signal, and store the digital signals for later processing, for telemetric transmission to an external device 954, or both. For example, the data acquisition system 952 may be coupled to the right atrial lead 804, the coronary sinus lead 806, the right ventricular lead 808 and other leads through the switch 926 to sample cardiac signals across any pair of desired electrodes.

The data acquisition system 952 also may be coupled to receive signals from other input devices. For example, the data acquisition system 952 may sample signals from a physiologic sensor 970 or other components shown in FIG. 9 (connections not shown).

The microcontroller 920 is further coupled to a memory 960 by a suitable data/address bus 962, wherein the programmable operating parameters used by the microcontroller 920 are stored and modified, as required, in order to customize the operation of the device 800 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 802 within each respective tier of therapy. One feature of the described embodiments is the ability to sense and store a relatively large amount of data (e.g., from the data acquisition system 952), which data may then be used for subsequent analysis to guide the programming of the device 800.

Advantageously, the operating parameters of the implantable device 800 may be non-invasively programmed into the memory 960 through a telemetry circuit 964 (e.g., transmitter 314 and receiver 302) in telemetric communication via communication link 966 (e.g., link 106) with the external device 954 (e.g., device 400), such as a programmer, transtelephonic transceiver, a diagnostic system analyzer or some other device. The microcontroller 920 activates the telemetry circuit 964 with a control signal (e.g., via bus 968). The telemetry circuit 964 advantageously allows intracardiac electrograms and status information relating to the operation of the device 800 (as contained in the microcontroller 920 or memory 960) to be sent to the external device 954 through an established communication link 966.

The device 800 can further include one or more physiologic sensors 970. In some embodiments the device 800 may include a "rate-responsive" sensor that may provide, for example, information to aid in adjustment of pacing stimulation rate according to the exercise state of the patient. One or more physiologic sensors 970 (e.g., a pressure sensor) may further be used to detect changes in cardiac output, changes in the physiological condition of the heart, or diurnal changes in activity (e.g., detecting sleep and wake states). Accordingly, the microcontroller 920 responds by adjusting the various pacing parameters (such as rate, AV Delay, V-V Delay, etc.) at which the atrial and ventricular pulse generators 922 and 924 generate stimulation pulses.

While shown as being included within the device 800, it is to be understood that a physiologic sensor 970 may also be external to the device 800, yet still be implanted within or carried by the patient. Examples of physiologic sensors that may be implemented in conjunction with the device 800 include sensors that sense respiration rate, pH of blood, ventricular gradient, oxygen saturation, blood pressure and so forth. Another sensor that may be used is one that detects activity variance, wherein an activity sensor is monitored diurnally to detect the low variance in the measurement corresponding to the sleep state. For a more detailed description of an activity variance sensor, the reader is directed to U.S. Pat. No. 5,476,483 (Bornzin et al.), issued Dec. 19, 1995, which patent is hereby incorporated by reference.

The one or more physiologic sensors 970 may optionally include one or more of components to help detect movement (via, e.g., a position sensor or an accelerometer) and minute ventilation (via an MV sensor) in the patient. Signals generated by the position sensor and MV sensor may be passed to the microcontroller 920 for analysis in determining whether to adjust the pacing rate, etc. The microcontroller 920 may thus monitor the signals for indications of the patient's position and activity status, such as whether the patient is climbing up stairs or descending down stairs or whether the patient is sitting up after lying down.

The device 800 additionally includes a battery 976 that provides operating power to all of the circuits shown in FIG. 9. For a device 800 which employs shocking therapy, the battery 976 is capable of operating at low current drains (e.g., preferably less than 10 µA) for long periods of time, and is capable of providing high-current pulses (for capacitor charging) when the patient requires a shock pulse (e.g., preferably, in excess of 2 A, at voltages above 200 V, for periods of 10 seconds or more). The battery 976 also desirably has a predictable discharge characteristic so that elective replacement time can be detected. Accordingly, the device 800 preferably employs lithium or other suitable battery technology.

The device 800 can further include magnet detection circuitry (not shown), coupled to the microcontroller 920, to detect when a magnet is placed over the device 800. A magnet may be used by a clinician to perform various test functions of the device 800 and to signal the microcontroller 920 that the external device 954 is in place to receive data from or transmit data to the microcontroller 920 through the telemetry circuit 964.

The device 800 further includes an impedance measuring circuit 978 that is enabled by the microcontroller 920 via a control signal 980. The known uses for an impedance measuring circuit 978 include, but are not limited to, lead impedance surveillance during the acute and chronic phases for proper performance, lead positioning or dislodgement; detecting operable electrodes and automatically switching to an operable pair if dislodgement occurs; measuring respiration or minute ventilation; measuring thoracic impedance for determining shock thresholds; detecting when the device 800 has been implanted; measuring stroke volume; and detecting the opening of heart valves, etc. The impedance measuring circuit 978 is advantageously coupled to the switch 926 so that any desired electrode may be used.

In the case where the device 800 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 920 further controls a shocking circuit 982 by way of a control signal 984. The shocking circuit 982 generates shocking pulses of low (e.g., up to 0.5 J), moderate (e.g., 0.5 J to 10 J), or high signal (e.g., 11 J to 40 J), as controlled by the microcontroller 920. Such shocking pulses are applied to the patient's heart 802 through, for example, two shocking electrodes and as shown in this embodiment, selected from the left atrial coil electrode 826, the RV coil electrode 832 and the SVC coil electrode 834. As noted above, the housing 900 may act as an active electrode in combination with the RV coil electrode 832, as part of a split electrical vector using the SVC coil electrode 834 or the left atrial coil electrode 826 (i.e., using the RV electrode as a common electrode), or in some other arrangement.

Cardioversion level shocks are generally considered to be of low to moderate signal level (so as to minimize pain felt by the patient), be synchronized with an R-wave, pertain to the treatment of tachycardia, or some combination of the above. Defibrillation shocks are generally of moderate to high signal level (i.e., corresponding to thresholds in the range of 5 J to 40 J), delivered asynchronously (since R-waves may be too disorganized), and pertaining exclusively to the treatment of fibrillation. Accordingly, the microcontroller 920 is capable of controlling the synchronous or asynchronous delivery of the shocking pulses.

As mentioned above, the device 900 includes several components that provide the communication functionality discussed herein. For example, the telemetry circuit 964 (e.g., a transceiver) may include one or more of the components of FIG. 3. Such components may include some or a portion of the receiver 302, the transmitter 314, and the communication processor 312. In addition, the thresholds 308 may be stored in the data memory 960.

The microcontroller 920 (e.g., a processor providing signal processing functionality) may, in some embodiments, implement or support the communication functionality discussed herein. For example, the timing control 932 may provide the functionality for the timers 318 and 326. In addition, the microcontroller may comprise an adaptive detector module 939 that may provide a portion or all of the functionality relating to the parameter adapter 322, the counters 316 and 328, the comparator 306, the threshold definer 334, the location determiner 324, the bandwidth adjust component 332, the interference identifier 320, the communication processor 312, and some of the components of the receiver 302.

It should be appreciated that various modifications may be incorporated into the disclosed embodiments based on the teachings herein. For example, the structure and functionality taught herein may be incorporated into different types of devices other than those types specifically described. In addition, various algorithms or techniques may be employed to provide a wake-up detection scheme.

It should be appreciated from the above that the various structures and functions described herein may be incorporated into a variety of apparatuses (e.g., a stimulation device, a monitoring device, etc.) and implemented in a variety of ways. Different embodiments of the stimulation device may include a variety of hardware and software processing components. In some embodiments, hardware components such as processors, controllers, state machines, logic, or some combination of these components, may be used to implement the described components or circuits.

In some embodiments, code including instructions (e.g., software, firmware, middleware, etc.) may be executed on one or more processing devices to implement one or more of the described functions or components. The code and associated components (e.g., data structures and other components by the code or to execute the code) may be stored in an appropriate data memory that is readable by a processing device (e.g., commonly referred to as a computer-readable medium).

The components and functions described herein may be connected or coupled in many different ways. The manner in which this is done may depend, in part, on whether and how the components are separated from the other components. In some embodiments some of the connections or couplings represented by the lead lines in the drawings may be in an integrated circuit, on a circuit board or implemented as discrete wires or in other ways.

The signals discussed herein may take various forms. For example, in some embodiments a signal may comprise electrical signals transmitted over a wire, light pulses transmitted through an optical medium such as an optical fiber or air, or RF waves transmitted through a medium such as air, etc. In addition, a plurality of signals may be collectively referred to as a signal herein. The signals discussed above also may take the form of data. For example, in some embodiments an application program may send a signal to another application program. Such a signal may be stored in a data memory.

Moreover, the recited order of the blocks in the processes disclosed herein is simply an example of a suitable approach. Thus, operations associated with such blocks may be rearranged while remaining within the scope of the present disclosure. Similarly, the accompanying method claims present operations in a sample order, and are not necessarily limited to the specific order presented.

While certain exemplary embodiments have been described above in detail and shown in the accompanying drawings, it is to be understood that such embodiments are merely illustrative of and not restrictive of the broad invention. In particular, it should be recognized that the teachings herein apply to a wide variety of apparatuses and methods. It will thus be recognized that various modifications may be made to the illustrated and other embodiments described above, without departing from the broad inventive scope thereof. In view of the above it will be understood that the invention is not limited to the particular embodiments or arrangements disclosed, but is rather intended to cover any changes, adaptations or modifications which are within the scope of the invention as defined by the appended claims.

What is claimed is:

1. A communication wake-up method for a medical device implanted within a patient, comprising:
    counting a quantity of times valid communication signals have been identified during a fully awakened mode of a staged signal detection scheme and/or a quantity of times valid communication signals have not been identified during a fully awakened mode of a stage signal detection scheme;
    adapting a signal detection parameter based on the count;
    invoking a partially awakened mode for at least one communication component to scan for at least one radio frequency signal;
    comparing a characteristic of the at least one radio frequency signal with at least one threshold; and
    invoking, based on a result of the comparison, a fully awakened mode for the at least one communication component to scan for a signal from an external device.

2. The method of claim 1, wherein the characteristic comprises amplitude, frequency, or phase.

3. The method of claim 1, wherein the comparison comprises amplitude detection, frequency demodulation, or phase-locking.

4. The method of claim 1, wherein the comparison comprises determining whether the at least one radio frequency signal has a sufficient amount of energy.

5. The method of claim 1, wherein the adaptation comprises adapting an amplification of the at least one radio frequency signal.

6. The method of claim 1, further comprising, after the fully awakened mode is invoked, determining whether a message received from the external device includes an identifier associated with the implanted medical device.

7. The method of claim 1, further comprising, after the fully awakened mode is invoked, transferring data between the implanted medical device and the external device.

8. The method of claim 1, further comprising monitoring ambient radio frequency signals to define the at least one threshold.

9. The method of claim 8, wherein the defined at least one threshold is associated with at least one of a group consisting of: a current location, a current time of day, and a current day.

10. The method of claim 9, further comprising communicating with the external device to define at least one time to monitor the radio frequency signals.

11. The method of claim 1, further comprising defining the at least one threshold based on information received from the external device.

12. The method of claim 1, wherein the comparing comprises comparing successive radio frequency signals with successively higher threshold values.

13. The method of claim 1, wherein:
    the at least one radio frequency signal comprises a plurality of radio frequency signals;
    the at least one threshold comprises a plurality of thresholds;
    if the comparison indicates that a characteristic of a first one of the radio frequency signals exceeds a first one of the thresholds, the comparison further comprises comparing a characteristic of a second one of the radio frequency signals with a second one of the thresholds; and
    the second one of the thresholds has a higher value than the first one of the thresholds.

14. The method of claim 1, wherein a scanning of the partially awakened mode comprises detecting successive radio frequency signals using successively narrower frequency bands.

15. The method of claim 1, wherein:
    the at least one radio frequency signal comprises a plurality of radio frequency signals each of which is associated with a different radio frequency band;
    if the comparison indicates that a characteristic of a first one of the radio frequency signals associated with a first one of the radio frequency bands exceeds a first one of the thresholds, the scanning of the partially awakened mode further comprises scanning a second one of the radio frequency signals associated with a second one of the radio frequency bands; and
    the second one of the radio frequency bands is narrower than the first one of the radio frequency bands.

16. The method of claim 1, wherein:
    a scanning of the partially awakened mode and the comparison are performed repeatedly to generate the comparison result; and
    whether the fully awakened state is invoked depends on how many of the comparisons indicate an acceptable signal characteristic.

17. The method of claim 1, wherein the radio frequency signal is scanned for in a radio frequency band which comprises at least a portion of a medical implant communication service band.

18. The method of claim 1, wherein determining whether the external device has transmitted a signal to the medical device comprises obtaining an identifier associated with the medical device from a signal received from the external device.

19. The method of claim 1, wherein the adaptation reduces power consumption of the implanted medical device.

20. The method of claim 1, wherein the adaptation optimizes a communication range of the device.

21. The method of claim 1, wherein the adaptation optimizes a wake-up time of the device.

22. The method of claim 1, wherein the adaptation reduces how often scanning is performed to determine whether the external device has transmitted a signal to the implanted medical device.

23. The method of claim 1, wherein the adaptation reduces how often scanning results in a determination that the external device has not transmitted a signal to the implanted medical device.

24. The method of claim 1, wherein the adaptation comprises adapting the at least one threshold.

25. The method of claim 24, wherein the adaptation of the at least one threshold comprises decreasing the at least one threshold if the determination indicates that the external device has not transmitted a signal to the implanted medical device.

26. The method of claim 24, wherein the adaptation of the at least one threshold comprises increasing the at least one threshold if the determination indicates that the external device has transmitted a signal to the implanted medical device.

27. The method of claim 24, further comprising adapting the at least one threshold based on at least one of the group consisting of: a current location, a current time of day, and a current day.

28. The method of claim 24, further comprising automatically adapting the at least one threshold back to at least one prior threshold value.

29. The method of claim 28, wherein the at least one threshold is automatically adapted back to the at least one prior threshold value after a defined period of time.

30. The method of claim 28, wherein the at least one threshold is automatically adapted back to the at least one prior threshold value if a magnitude of an interfering signal has decreased.

\* \* \* \* \*